US012708624B2

(12) United States Patent
Burns et al.

(10) Patent No.: US 12,708,624 B2
(45) Date of Patent: Aug. 18, 2026

(54) METHODS OF TREATING PULMONARY FIBROSIS

(71) Applicant: Amplia Therapeutics Limited, Melbourne (AU)

(72) Inventors: Chris Burns, Melbourne (AU); John Lambert, Melburne (AU); Mark Graeme Devlin, Melbourne (AU)

(73) Assignee: Amplia Therapeutics Limited, Melbourne (AU)

( * ) Notice: Subject to any disclaimer, the term of this patent is extended or adjusted under 35 U.S.C. 154(b) by 674 days.

(21) Appl. No.: 17/926,114

(22) PCT Filed: May 17, 2021

(86) PCT No.: PCT/AU2021/050457

§ 371 (c)(1),
(2) Date: Nov. 17, 2022

(87) PCT Pub. No.: WO2021/237273

PCT Pub. Date: Dec. 2, 2021

(65) Prior Publication Data

US 2023/0190746 A1 Jun. 22, 2023

(30) Foreign Application Priority Data

May 28, 2020 (AU) ................................ 2020901743

(51) Int. Cl.
*A61K 31/506* (2006.01)
*A61P 11/00* (2006.01)

(52) U.S. Cl.
CPC ............ *A61K 31/506* (2013.01); *A61P 11/00* (2018.01)

(58) Field of Classification Search
CPC .... A61K 31/4545; A61K 31/506; A61P 11/00
See application file for complete search history.

(56) References Cited

U.S. PATENT DOCUMENTS

| | | | |
|---|---|---|---|
| 8,377,938 | B2 | 2/2013 | Matsushima |
| 12,466,807 | B2 | 11/2025 | Burns et al. |
| 2010/0113475 | A1 | 5/2010 | Adams et al. |
| 2022/0340540 | A1 | 10/2022 | Burns et al. |
| 2025/0282751 | A1 | 9/2025 | Burns et al. |

FOREIGN PATENT DOCUMENTS

| | | | |
|---|---|---|---|
| JP | 2015520243 | A | 7/2015 |
| WO | 199722596 | A1 | 6/1997 |
| WO | 199730035 | A1 | 8/1997 |
| WO | 199732856 | A1 | 9/1997 |
| WO | 199813354 | A1 | 4/1998 |
| WO | 199835985 | A1 | 8/1998 |
| WO | 199902166 | A1 | 1/1999 |
| WO | 200040529 | A1 | 7/2000 |
| WO | 200041669 | A2 | 7/2000 |
| WO | 200047212 | A1 | 8/2000 |
| WO | 200132651 | A1 | 5/2001 |
| WO | 200160814 | A2 | 8/2001 |
| WO | 200192224 | A1 | 12/2001 |
| WO | 200204434 | A1 | 1/2002 |
| WO | 200208213 | A1 | 1/2002 |
| WO | 2008023698 | A1 | 2/2008 |
| WO | 2008115369 | A2 | 9/2008 |
| WO | 2008129380 | A1 | 10/2008 |
| WO | 2009024332 | A1 | 2/2009 |
| WO | 2009105498 | A1 | 8/2009 |
| WO | 2010058030 | A1 | 5/2010 |
| WO | 2010058032 | A2 | 5/2010 |
| WO | 2012022408 | A1 | 2/2012 |
| WO | 2012110774 | A1 | 8/2012 |
| WO | 2013192556 | A2 | 12/2013 |
| WO | 2014027199 | A1 | 2/2014 |

(Continued)

OTHER PUBLICATIONS

PubChem, CID 60162119, record created Sep. 19, 2012 (Year: 2012).*

Venkataraman et. al., Antiviral Res., vol. 143, pp. 142-150, publ. 2017 (Year: 2017).*

Bastin, R. J. et al, (2000). "Salt Selection and Optimization Procedures for Pharmaceutical New Chemical Entities," Organic Process Research & Development 4(5):427-435.

Hirayama, N. (2008). Yukikagobutsu Kessho Sakusei Handobukku (handbook for preparation of organic compound crystals), pp. 17-23, 37-40, 45-51, 57-65. (Explanation of Relevance of Reference No. 5 listed in Japanese Office Action, pp. 2, 3, and 4), 35 pages.

Wermuth, C.G. (1999). The Practice of Medicinal Chemistry, second volume, p. 347-365, Technomics, Inc., (Explanation of Relevance of Reference No. 2 listed in Japanese Notice of Reasons for Rejection Office Action, pp. 2, 3, and 4.), total pages 27.

Amplia Therapeutics (May 19, 2020). "FDA Awards Amplia Orphan Drug Designation for Idiopathic Pulmonary Fibrosis," ASX Release, 2 pages.

(Continued)

*Primary Examiner* — Sarah Pihonak

(74) *Attorney, Agent, or Firm* — MORRISON & FOERSTER LLP

(57) ABSTRACT

A method of treating or preventing pulmonary fibrosis in a patient in need thereof by administering a FAK inhibitor defined by formula I or a pharmaceutically acceptable derivative thereof to said patient: (I)

Formula I

4 Claims, 6 Drawing Sheets

(56) References Cited

FOREIGN PATENT DOCUMENTS

WO 2020191448 A1 10/2020
WO 2021237273 A1 12/2021

OTHER PUBLICATIONS

Carvalho, J. (May 20, 2020). "FDA Names AMP945, Potential IPF Treatment, an Orphan Drug," located at https://pulmonaryfibrosisnews.com/news/fda-names-amp945-potential-idiopathic-pf-treatment-orphan-drug/?cn-reloaded=1, last visited on Jun. 17, 2024, six pages.
Lagares, D. et al. (May 2012). "Inhibition of Focal Adhesion KinasePrevents Experimental Lung Fibrosis and Myofibroblast Formation," Arthritis & Rheumatism 64(5):1653-1664.
Balbach, S. et al. (2004). "Pharmaceutical Evaluation Of Early Development Candidates "The 100 Mg-Approach"," International Journal of Pharmaceutics 275(1-2):1-12, 20 pages.
Golas, J.M. et al. (Jan. 15, 2003). "SKI-606, A 4-Anilino-3-Quinolinecarbonitrile Dual Inhibitor Of Src And Abl Kinases, Is A Potent Antiproliferative Agent Against Chronic Myelogenous Leukemia Cells In Culture And Causes Regression Of K562 Xenografts In Nude Mice," Cancer Research 63(2):375-381.
International Search Report and Written Opinion of the Searching Authority mailed on May 4, 2020, for Patent Application No. PCT/AU2020/050292, 11 pages.
Lombardo, L.J. et al. (Dec. 1, 2004). "Discovery Of N-(2-Chloro-6-Methyl-Phenyl)-2-(6-(4-(2-Hydroxyethyl)-Piperazin-1-Yl)-2-Methylpyrimidin-4-Ylamino) Thiazole-5-Carboxamide (BMS-354825), A Dual Src/Abl Kinase Inhibitor With Potent Antitumor Activity In Preclinical Assays," Journal Of Medicinal Chemistry 47(27):6658-6661.
Stern, M. et al. (Apr. 1, 2005). "Overview Of Monoclonal Antibodies In Cancer Therapy: Present And Promise," Critical Reviews In Oncology/Hematology 54(1):11-29.
Crestani, B. et al. (2019, e-pub. Sep. 14, 2018). "Long-Term Safety And Tolerability Of Nintedanib In Patients With Idiopathic Pulmonary Fibrosis: Results From The Open-Label Extension Study, INPULSIS-ON," The Lancet Respiratory Medicine 7(1):60-68.
Evans, C. M. et al. (2016). "Idiopathic Pulmonary Fibrosis: A Genetic Disease That Involves Mucociliary Dysfunction Of The Peripheral Airways," Physiological Reviews 96(4):1567-1591, 27 pages.
1. Flaherty, K.R. et al. (2021). "Nintedanib In Progressive Fibrosing Interstitial Lung Diseases," Eur. Respir., 1718-1727, 27 pages.
George, P. M. et al. (Aug. 2020, e-pub. May 15, 2020). "Pulmonary Fibrosis And COVID-19: The Potential Role For Antifibrotic Therapy," The Lancet Respiratory Medicine 8(8):807-815.
International Search Report and Written Opinion mailed Jun. 11, 2021, for PCT Patent Application No. PCT/AU2021/050457, filed May 12, 2021, 11 pages.
Kato, M. et al. (2019, e-pub. Aug. 19, 2019). "Gastrointestinal Adverse Effects Of Nintedanib And The Associated Risk Factors In Patients With Idiopathic Pulmonary Fibrosis," Scientific Reports 9(1):1-9.
King Jr., T. E. et al. (May 29, 2014). "A Phase 3 Trial Of Pirfenidone In Patients With Idiopathic Pulmonary Fibrosis," New England Journal Of Medicine 370(22):2083-2092.
Kinoshita, K. et al. (May 3, 2013). "Antifibrotic Effects of Focal Adhesion Kinase Inhibitor in Bleomycin-Induced Pulmonary Fibrosis in Mice," American Journal Of Respiratory Cell And Molecular Biology 49(4):536-543.
Kärkkäinen, M. et al. (Aug. 22, 2017). "Effect Of Smoking And Comorbidities On Survival In Idiopathic Pulmonary Fibrosis," Respiratory Research 18(1):1-10.
Lagares, D. et al. (2013, e-pub. Nov. 27, 2012). "Targeting Focal Adhesion Kinase In Fibrotic Diseases," Biodrugs 27(1):15-23.
Lancaster, L. et al. (2019). "Safety And Survival Data In Patients With Idiopathic Pulmonary Fibrosis Treated With Nintedanib: Pooled Data From Six Clinical Trials," BMJ Open Respiratory Research 6(1):e000397, 7 pages.
Lancaster, L. H. et al. (2017). "Pirfenidone Safety And Adverse Event Management In Idiopathic Pulmonary Fibrosis," European Respiratory Review 26(146):10 Pages.
Maher, T. M. et al. (2019). "Antifibrotic Therapy For Idiopathic Pulmonary Fibrosis: Time To Treat," Respiratory Research 20(205):1-9.
Martinez, F. J. et al. (2017, e-pub. Oct. 20, 2017). "Idiopathic Pulmonary Fibrosis," Nature Reviews Disease Primers 3(17074):1-19.
Mercer, P. F. et al. (2013, e-pub. Jan. 5, 2013). "Coagulation And Coagulation Signalling In Fibrosis," Biochimica Et Biophysica Acta (BBA)—Molecular Basis of Disease 1832(7):1018-1027.
Raghu, G. et al. (Jul. 2014, e-pub. May 27, 2014). "Idiopathic Pulmonary Fibrosis In US Medicare Beneficiaries Aged 65 Years And Older: Incidence, Prevalence, And Survival, 2001-2011," The Lancet Respiratory Medicine 2(7):566-572, 10 pages.
Richeldi, L. et al. (2020). "Efficacy And Safety Of Nintedanib In Idiopathic Pulmonary Fibrosis," New England Journal Of Medicine 20:3, 8 pages.
Roberts, W. G. et al. (Mar. 15, 2008). "Antitumor Activity And Pharmacology Of A Selective Focal Adhesion Kinase Inhibitor, PF-562,271," Cancer Research 68(6):1935-1944.
Russell, A. M. et al. (Oct. 15, 2016). "Daily Home Spirometry: An Effective Tool For Detecting Progression In Idiopathic Pulmonary Fibrosis," American Journal Of Respiratory And Critical Care Medicine 194(8):989-997.
Taskar, V.S. et al. (2006). "Is Idiopathic Pulmonary Fibrosis An Environmental Disease?," Proceedings Of The American Thoracic Society 3(4):293-298.
Van Manen, M. J. et al. (2017). "Optimizing Quality Of Life In Patients With Idiopathic Pulmonary Fibrosis," Therapeutic Advances in Respiratory Disease 11(3):157-169.
Visca, D. et al. (2018). "Effect Of Ambulatory Oxygen On Quality Of Life For Patients With Fibrotic Lung Disease (Ambox): A Prospective, Open-Label, Mixed-Method, Crossover Randomised Controlled Trial," The Lancet Respiratory Medicine 6(10):759-770.
Wang, Z. G. et al. (2008). "TAE226, A Dual Inhibitor For FAK And IGF-IR, Has Inhibitory Effects On Mtor Signaling In Esophageal Cancer Cells," Oncology Reports 20(6):1473-1477.
Zhao, X. K. et al. (Jan. 14, 2016). "Focal Adhesion Kinase Regulates Fibroblast Migration Via Integrin Beta-1 And Plays A Central Role In Fibrosis," Scientific Reports 6(19276):1-12.
Berge, S.M. et al. (Jan. 1977). "Pharmaceuticals Salts," J. Pharmaceutical Sciences 66(1):1-19.
Gupta, D. et al. (Jul. 14, 2018). "Salts Of Therapeutic Agents: Chemical, Physicochemical, And Biological Considerations," Molecules 23(7):1719, 15 pages.
Thompson, D. C. et al. (1992). "Biological And Toxicological Consequences Of Quinone Methide Formation," Chemical-Biological Interactions 86:129-162.
Zamora, A. C. et al. (2024, e-pub. May 19, 2024). "When The Third Time Is Not The Charm—Trial Outcomes In Idiopathic Pulmonary Fibrosis," JAMA:E1-E3.
FDA. "Search Orphan Drug Designations and Approvals: Benzeneacetamide, 2-[2-[2-[2-methoxy-4-(1-methyl-4-piperidinyl) phenyl]amino]-5-(trifluoromethyl)-4-pyrimidinyl]ethyl]-," FDA U.S. Food and Drug Administration, retrieved from the Internet via the Wayback Machine https://web.archive.org/web/20200525195732/https:/www.accessdata.fda.gov/scripts/opdlisting/oopd/detailedIndex.cfm?cfgridkey=742020, last visited May 25, 2020, 2 pages.
FDA. "Search Orphan Drug Designations and Approvals: Results for All Drug Designations," FDA U.S. Food and Drug Administration, retrieved from the Internet via the Wayback Machine https://web.archive.org/web/20200525195732/https:/www.accessdata.fda.gov/scripts/opdlisting/oopd/detailedIndex.cfm?cfgridkey=742020, last visited May 25, 2020, 2 pages.

* cited by examiner

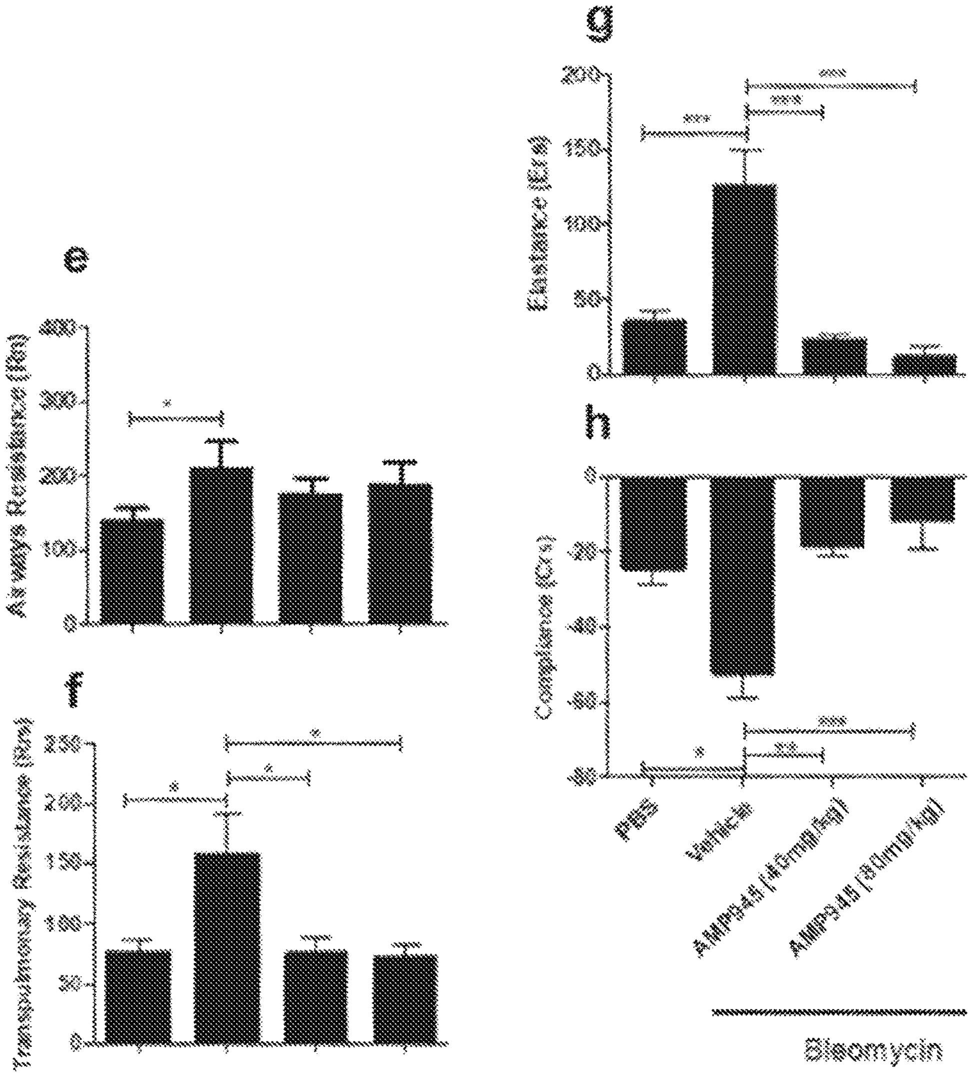
Figure 5 - continued

METHODS OF TREATING PULMONARY FIBROSIS

CROSS REFERENCE TO RELATED APPLICATIONS

This application is a national stage application under 35 U.S.C. § 371 of International Application No. PCT/AU2021/050457, filed internationally on May 17, 2021, which claims the benefit priority of Australian Application No. 2020901743, filed on May 28, 2020.

FIELD OF THE INVENTION

The present invention is directed to methods of treating or preventing pulmonary fibrosis (preferably idiopathic pulmonary fibrosis or pulmonary fibrosis associated with a coronavirus infection) in a patient in need thereof by administering a FAK inhibitor defined by formula I below or a salt or prodrug thereof to said patient:

Formula I

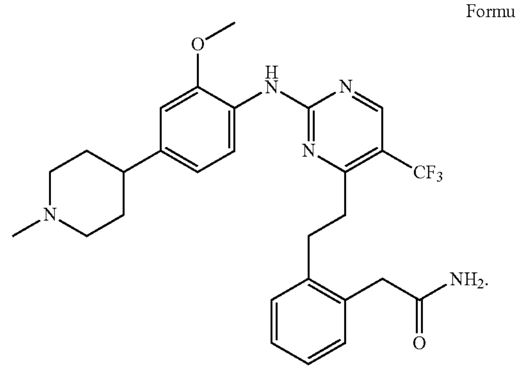

BACKGROUND OF THE INVENTION

Patients with a spectrum of lung disorders, including idiopathic pulmonary fibrosis (IPF), have a progressive fibrosing clinical phenotype that is characterized by an increasing extent of fibrosis on high-resolution computed tomography (CT), decline in lung function, worsening of symptoms and quality of life, and early death despite current therapy. On the basis of the clinical and pathophysiological similarities among these diseases, it has been postulated that such disorders with a progressive phenotype have a common pathobiologic mechanism regardless of the cause and thus could all respond to similar treatment (1).

Idiopathic pulmonary fibrosis (IPF) is a rare progressive disease, mainly in older adults and is characterized by chronic and progressive fibrosing of the lung interstitium leading to exertion-related breathlessness, cough, dyspnea and worsening lung function (2).

As the name suggests, the disease has no known cause and while the clinical course is variable, the prognosis is exceptionally poor. An analysis of US Medicare claims indicated that increased age and male gender were associated with increased incidence of IPF (3). Other risk factors include a history of smoking (4), occupational exposures (5) and certain viral infections (2). Without antifibrotic treatment there is a median survival time from diagnosis of approximately 3 years (6). Given the low survival rates, new therapies are needed but IPF is notoriously resistant to pharmacological intervention.

The Genetics Home Reference estimates that about 30,000 to 40,000 new cases of IPF are diagnosed in the United States each year (7). The incidence and prevalence of IPF increases significantly with age and it has been estimated that in the United States the population prevalence of IPF is 130,000 (1).

Deterioration of forced vital capacity (FVC) is a clinical hallmark of IPF (8) and, in clinical studies, the antifibrotic agents nintedanib and pirfenidone have been shown to slow the deterioration in forced vital capacity FVC caused by IPF (9). Notably, nintedanib and pirfenidone are only able to slow the slow the progression of IPF, decreasing the rate of deterioration of lung function without reversing disease progression.

In patients with mild or moderate FVC impairment at baseline, nintedanib and pirfenidone have shown a reduction in the rate of decline in FVC by approximately 50% over 1 year of treatment (10, 11). Extended treatment with nintedanib for up to four years also demonstrated a sustained decline in deterioration of FVC (12). Despite these promising results, uptake in clinical prescription of nintedanib and pirfenidone has been slow, primarily due to their relatively marginal impact on the slowing of disease progression and these drugs' side effect profiles. Side effects of pirfenidone include diarrhea, photosensitivity and rash (13), while nausea and diarrhea are the most common adverse effects of nintedanib in patients with IPF (14).

In addition to nintedanib and pirfenidone, clinical guidelines recommend holistic disease management (15) including pulmonary rehabilitation, symptom management, vaccinations, management of comorbidities and supplemental oxygen (16).

Although nintedanib and pirfenidone have improved the management of IPF, new therapies are required.

Furthermore such therapies may be useful in managing coronavirus infections as data from previous coronavirus infections such as severe acute respiratory syndrome and Middle East respiratory syndrome, as well as emerging data from the COVID-19 pandemic, suggest there could be substantial fibrotic consequences following SARS-CoV-2 infection. Antifibrotic therapies that are available or in development could have value in preventing severe COVID-19 in patients with IPF, have the potential to treat severe COVID-19 in patients without IPF, and might have a role in preventing fibrosis after SARS-CoV-2 infection (17).

1 Flaherty, K. R., 'Nintedanib in Progressive Fibrosing Interstitial Lung Diseases', N Engl J Med 2019; 381: 1718-27.

2 Martinez, F. J., et al., 'Idiopathic Pulmonary Fibrosis', Nat Rev Dis Primers, 3 (2017), 17074

3 Raghu, G., et al., 'Idiopathic Pulmonary Fibrosis in Us Medicare Beneficiaries Aged 65 Years and Older: Incidence, Prevalence, and Survival, 2001-11', Lancet Respir Med, 2 (2014), 566-72.

4 Karkkainen, M., et al., 'Effect of Smoking and Comorbidities on Survival in Idiopathic Pulmonary Fibrosis', Respir Res, 18 (2017), 160.

5 Taskar, V. S., and Coultas, D. B., 'Is Idiopathic Pulmonary Fibrosis an Environmental Disease?', Proc Am Thorac Soc, 3 (2006), 293-8.

6 Lancaster, L., et al., 'Safety and Survival Data in Patients with Idiopathic Pulmonary Fibrosis Treated with Nintedanib: Pooled Data from Six Clinical Trials', BMJ Open Respir Res, 6 (2019), e000397.

7 GeneticsHomeReference, 'Idiopathic Pulmonary Fibrosis', National Institutes of Health, (2020) <https://ghr.nlm.nih.gov/condition/idiopathic-pulmonary-fibrosis#statistics> [Accessed 13 Feb. 2020 2020].

8 Russell, A. M., et al., 'Daily Home Spirometry: An Effective Tool for Detecting Progression in Idiopathic Pulmonary Fibrosis', Am J Respir Crit Care Med, 194 (2016), 989-97.

9 Maher, T. M., and Strek, M. E., 'Antifibrotic Therapy for Idiopathic Pulmonary Fibrosis: Time to Treat', Respir Res, 20 (2019), 205.

10 King, T. E., Jr., et al., 'A Phase 3 Trial of Pirfenidone in Patients with Idiopathic Pulmonary Fibrosis', N Engl J Med, 370 (2014), 2083-92.

11 Richeldi, L., et al., 'Efficacy and Safety of Nintedanib in Idiopathic Pulmonary Fibrosis', N Engl J Med, 370 (2014), 2071-82.

12 Crestani, B., et al., 'Long-Term Safety and Tolerability of Nintedanib in Patients with Idiopathic Pulmonary Fibrosis: Results from the Open-Label Extension Study, Inpulsis-On', Lancet Respir Med, 7 (2019), 60-68.

13 Lancaster, L. H., et al., 'Pirfenidone Safety and Adverse Event Management in Idiopathic Pulmonary Fibrosis', Eur Respir Rev, 26 (2017).

14 Kato, M., et al., 'Gastrointestinal Adverse Effects of Nintedanib and the Associated Risk Factors in Patients with Idiopathic Pulmonary Fibrosis', Sci Rep, 9 (2019), 12062.

15 van Manen, M. J., et al., 'Optimizing Quality of Life in Patients with Idiopathic Pulmonary Fibrosis', Ther Adv Respir Dis, 11 (2017), 157-69.

16 Visca, D., et al., 'Effect of Ambulatory Oxygen on Quality of Life for Patients with Fibrotic Lung Disease (Ambox): A Prospective, Open-Label, Mixed-Method, Crossover Randomised Controlled Trial', Lancet Respir Med, 6 (2018), 759-70.

17. George, P., et al., 'Pulmonary fibrosis and COVID-19: the potential role for antifibrotic therapy', Lancet Respir Med (2020), https://doi.org/10.1016/S2213-2600 (20) 30225-3.

18. Mercer, P. F., and Chambers, R. C., 'Coagulation and Coagulation Signalling in Fibrosis', Biochim Biophys Acta, 1832 (2013), 1018-27.

19. Lagares, D., and Kapoor, M., 'Targeting Focal Adhesion Kinase in Fibrotic Diseases', BioDrugs, 27 (2013), 15-23.

SUMMARY OF THE INVENTION

The present inventors have found that the FAK (focal adhesion kinase) inhibitor of formula I (which is the third example of the thirteen examples presented in WO2012110774) is surprisingly selective for FAK when compared to other kinases (and therefore is less likely to show off-target effects associated with toxicity) and shows efficacy in the treatment of pulmonary fibrosis, particularly idiopathic pulmonary fibrosis.

The term "pulmonary fibrosis" as used herein refers to any one of a spectrum of lung disorders, including idiopathic pulmonary fibrosis (IPF), having a progressive fibrosing clinical phenotype that is characterized by an increasing extent of fibrosis on high-resolution computed tomography (CT), decline in lung function, worsening of symptoms and quality of life, and early death despite current therapy.

The term "infection with a coronavirus" includes but is not limited to infection with a coronavirus associated with severe acute respiratory syndrome (SARS), Middle East respiratory syndrome (MERS), as well as COVID-19 (SARS-CoV-2).

Accordingly, in a first embodiment, there is provided a method of treating or preventing pulmonary fibrosis in a patient in need thereof by administering a FAK inhibitor defined by formula I below or a pharmaceutically acceptable derivative thereof to said patient:

Formula I

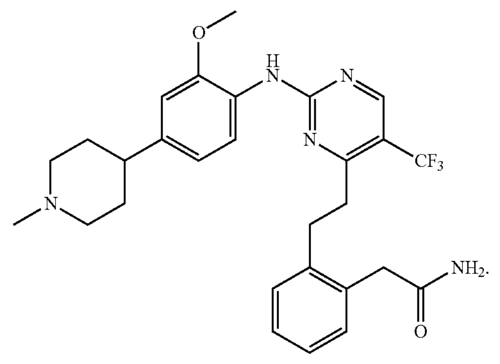

Preferably, the salt is a tartrate salt.

In a second embodiment, there is provided a FAK inhibitor defined by formula I or a pharmaceutically acceptable derivative thereof for use in the treatment of pulmonary fibrosis in a patient in need thereof.

In a third embodiment, there is provided the use of a FAK inhibitor defined by formula I or a pharmaceutically acceptable derivative thereof in the manufacture of a medicament for treating or preventing pulmonary fibrosis in a patient in need thereof.

In a preferred form, the pulmonary fibrosis is idiopathic pulmonary fibrosis (IPF).

In another preferred from, the pulmonary fibrosis is associated with infection by a coronavirus, particularly a coronavirus associated with COVID-19 (SARS-CoV-2).

DETAILED DESCRIPTION OF THE EMBODIMENTS

Figure 1:
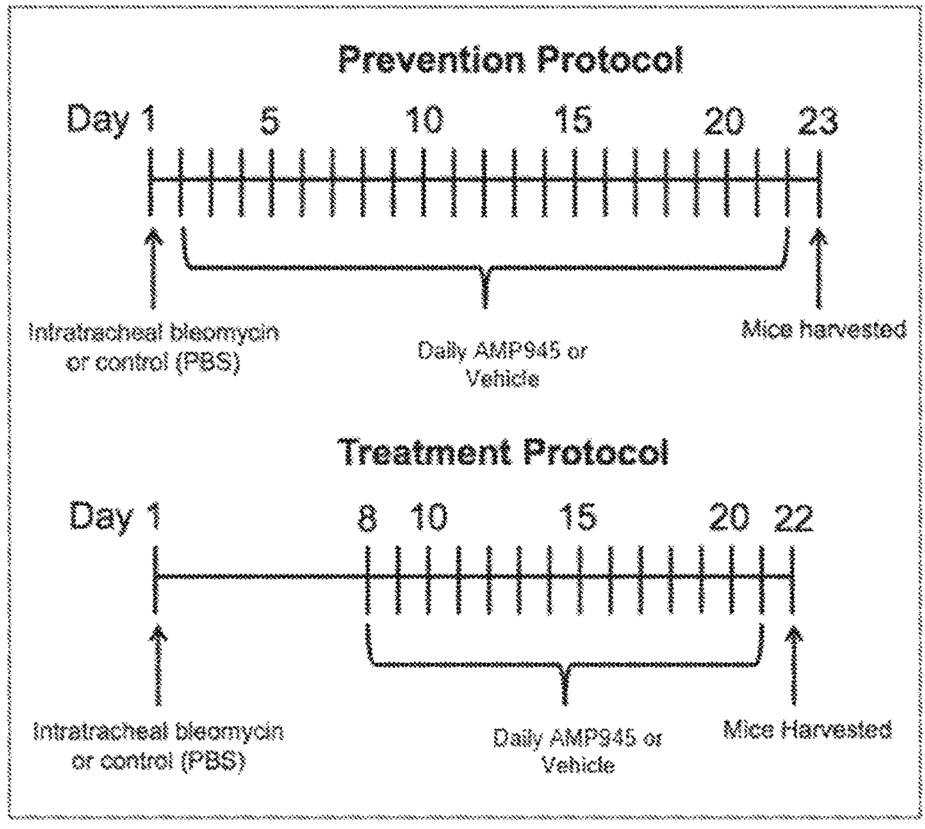
FIG. 1. Protocols used to assess the ability of the compound of Formula I to prevent or treat lung fibrosis induced by intratracheal bleomycin (30 μl; 0.05 U/mouse) or PBS (30 μl; vehicle control).

The compound of Formula I is a potent and selective small molecule inhibitor of focal adhesion kinase (FAK). In a biochemical assay, the IC50 of the compound of formula I for FAK was shown to be 2.2 nM while in a cellular assay using MDA-231 LNA cells, the IC50 was determined to be 7 nM. Surprisingly, in a KINOMEScan™ assay which assessed the relative inhibitory potency of the compound of formula I compared to 467 other kinases, the compound of formula I tested at a concentration of 1 micromolar, was found to have a S10 selectivity score of 0.02, making it a highly selective inhibitor of FAK relative to other kinases.

These studies show that the compound of Formula I is the most potent and selective FAK inhibitor described particularly when compared to other known FAK inhibitors such as PF-562,271 or TAE226 both of which have significant off-target kinase activity (see Roberts W G, Ung E, Whalen P, Cooper B, Hulford C, Autry C, Richter D, Emerson E, Lin J, Kath J, et al. Antitumor activity and pharmacology of a selective focal adhesion kinase inhibitor, PF-562,271. Cancer Res 2008; 68(6):1935-1944 (for PF-562,271), and Wang Z G, Fukazawa T, Nishikawa T, Watanabe N, Sakurama K, Motoki T, Takaoka M, Hatakeyama S, Omori O, Ohara T, et al. TAE226, a dual inhibitor for FAK and IGF-IR, has inhibitory effects on mTOR signaling in esophageal cancer cells. Oncol Rep 2008; 20(6):1473-14770 (for TAE226).

The compound of formula I has been shown to exhibit drug-like properties in that it shows dose-proportional exposures following oral dosing in rats, mice and dogs; possesses no detectable inhibition of common cytochrome P450s and displays no unique metabolites upon exposure to human, rat, dog or primate hepatocytes. The L-tartrate salt of the compound of Formula I is one proposed drug substance and this salt form has proven sufficiently soluble for use in preclinical studies without the need for addition of novel excipients or dissolution agents. Stability studies of the L-tartrate salt of the compound of Formula I have shown no significant degradation after 9 months under both long-term and accelerated conditions.

The compound has been shown to be effective in models of pulmonary fibrosis.

Without being bound by theory, the present inventors believe that the following rationale explains the reason for the effectiveness of the compound of Formula I.

Deposition of collagen, fibrin and other components of the extracellular matrix is an integral part of wound healing and normal tissue repair. However, in the setting of chronic inflammatory diseases, the persistent activity of myofibroblast cells recruited to the site of inflammation or differentiated from mesenchymal precursors can lead to excessive and sustained fibrous connective tissue deposition resulting in organ scarring, malfunction and death (18). In recent years, a growing understanding of the cellular and molecular mechanisms underlying fibrosis have provided a rationale for the therapeutic targeting of specific effector cells and signaling pathways in the fibrotic cascade.

Focal adhesion kinase (FAK) is a non-receptor tyrosine kinase that plays a key role in a variety of cellular processes, in particular those related to the adhesion and migration of most cell types. The structure of the FAK protein allows it to interact with cell surface receptors of several classes such as integrins, G protein-coupled receptors (GPCRs) and receptor tyrosine kinases (RTKs), on the one hand, and the actin cytoskeleton through adapter proteins such as talin and paxillin, on the other (19). Consistent with these functions, FAK is important in transducing chemotactic and haptotactic stimuli from the extracellular environment and orchestrating changes in cellular adhesion and motility in response to these signals. In addition to these functions, dimerization of FAK in response to integrin clustering at the cell surface permits autophosphorylation of Y397, docking of Src and the activation of cell signaling pathways, including the PI3K/Akt pathway.

FAK has been shown to contribute to multiple mechanisms underlying fibrosis (19) and taken together, this evidence provides a strong biological rationale for targeting FAK for the treatment and prevention of fibrotic diseases of the lung and other tissues.

The term "pharmaceutically acceptable derivative" may include any pharmaceutically acceptable salt, hydrate or prodrug, or any other compound which upon administration to a subject, is capable of providing (directly or indirectly) a compound of formula I or an active metabolite or residue thereof.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

General information on types of pharmaceutically acceptable salts and their formation is known to those skilled in the art and is as described in general texts such as "Handbook of Pharmaceutical salts" P. H. Stahl, C. G. Wermuth, 1st edition, 2002, Wiley-VCH.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition.

The term "prevention" means use of the compound of Formulation I as a prophylactic measure (i.e. prophylaxis) in a patient susceptible to pulmonary fibrosis.

The compound of Formula I or pharmaceutical composition comprising the compound of Formula I may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

While it is possible for the compound of formula I to be administered alone, it is preferable to present it as a pharmaceutical composition (e.g. formulation) comprising at least the compound of formula I, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides use in the method of pharmaceutical compositions.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, Remington's Pharmaceutical Sciences, 18th edition, Mack Publishing Company, Easton, Pa., 1990.

The formulations may conveniently be presented in unit dosage form and may be prepared by any methods well known in the art of pharmacy. Such methods include the step of bringing into association the tartrate salt with the carrier which constitutes one or more accessory ingredients. In general, the formulations are prepared by uniformly and intimately bringing into association the tartrate salt with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the tartrate salt; as a powder or granules; as a solution or suspension in an aqueous or non-aqueous liquid; or as an oil-in-water liquid emulsion or a water-in-oil liquid emulsion; as a bolus; as an electuary; or as a paste.

Preferably, the formulation is suitable for oral administration.

A tablet may be made by conventional means, e.g., compression or moulding, optionally with one or more accessory ingredients. Compressed tablets may be prepared by compressing in a suitable machine the tartrate salt in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxy methyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the tartrate salt therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with the tartrate salt and optionally one or more excipients or diluents.

Formulations suitable for topical administration in the mouth include losenges comprising the tartrate salt in a flavoured basis, usually sucrose and acacia or tragacanth; pastilles comprising the tartrate salt in an inert basis such as gelatin and glycerin, or sucrose and acacia; and mouthwashes comprising the tartrate salt in a suitable liquid carrier.

Formulations suitable for topical administration to the eye also include eye drops wherein the tartrate salt is dissolved or suspended in a suitable carrier, especially an aqueous solvent for the tartrate salt.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the tartrate salt.

Formulations suitable for administration by inhalation include those presented as an aerosol spray from a pressurised pack, with the use of a suitable propellant, such as dichlorodifluoromethane, trichlorofluoromethane, dichorotetrafluoroethane, carbon dioxide, or other suitable gases.

Formulations suitable for topical administration via the skin include ointments, creams, and emulsions. When formulated in an ointment, the tartrate salt may optionally be employed with either a paraffinic or a water-miscible ointment base. Alternatively, the tartrate salt may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the tartrate salt through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat.

Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the tartrate salt in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the tartrate salt, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the tartrate salt in the solution is from about 1 ng/ml to about 10 μg/ml, for example from about 10 ng/ml to about 1 pg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the tartrate salt to blood components or one or more organs.

It will be appreciated that appropriate dosages of the tartrate salt, and compositions comprising the tartrate salt, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment.

Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the compound of formula I is in the range of about 100 pg to about 250 mg per kilogram body weight of the subject per day.

In a preferred form, a suitable dose of the compound of Formula I is 40 mg/kg.

It will be understood that the invention disclosed and defined in this specification extends to all alternative combinations of two or more of the individual features mentioned or evident from the text or drawings. All of these different combinations constitute various alternative aspects of the invention.

EXAMPLES

The invention will now be described by reference to the following non-limiting examples.

The Compound of Formula I in Preclinical Disease Models:

The efficacy of the compound of Formula I in both the treatment and prevention of bleomycin-induced lung fibrosis has been shown in studies designed by the present inventors. Study designs for the treatment and prevention experiments are shown in FIG. 1.

Lung fibrosis in female C57BL/6 mice aged between 6-8 weeks (ARC, Perth, Australia) was induced by a single intra-tracheal dose of bleomycin (0.05 U/mouse). Control mice received 30 μl of buffered saline.

Mice in the prevention study were dosed orally once daily from 24 hours post bleomycin administration until day 22 with either 200 μl of vehicle (Sterile water containing 0.5% (w/v) hydroxypropylmethylcellulose, 0.5% (v/v) benzyl alcohol and 0.4% (v/v) Tween 80), or the compound of Formula I at a dosage of 40 mg/kg or 80 mg/kg by oral gavage.

Mice in the treatment study were dosed once daily from day 7 post bleomycin administration until day 21 with either 200 μl of vehicle (Sterile water containing 0.5% (w/v) hydroxypropylmethylcellulose, 0.5% (v/v) benzyl alcohol and 0.4% (v/v) Tween 80) or the compound of Formula I at a dosage of 40 mg/kg or 80 mg/kg by oral gavage.

There were eight mice per group for all experiments and all mice were weighed daily during administration of the treatments.

Figure 2:
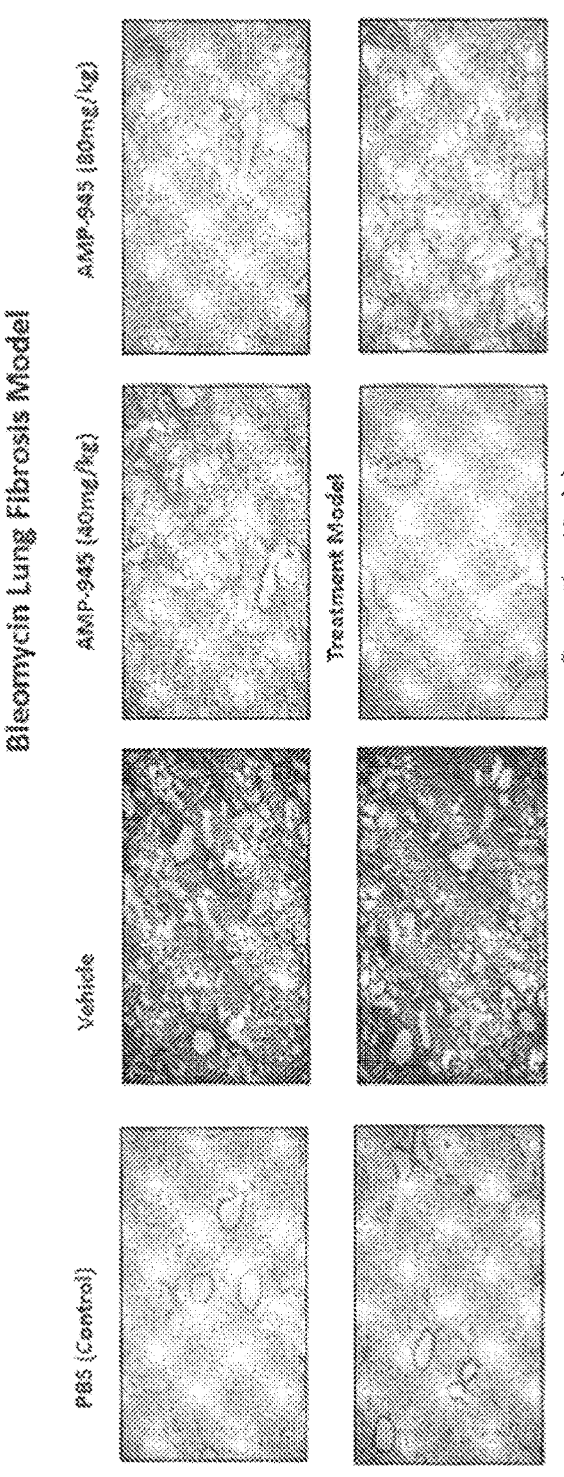
FIG. 2. Lung fibrosis assessed by Masson's trichrome staining (magnification ×20). Top panels: Treatment protocol. Bottom Panels: Prevention Protocol.
Figure 3:
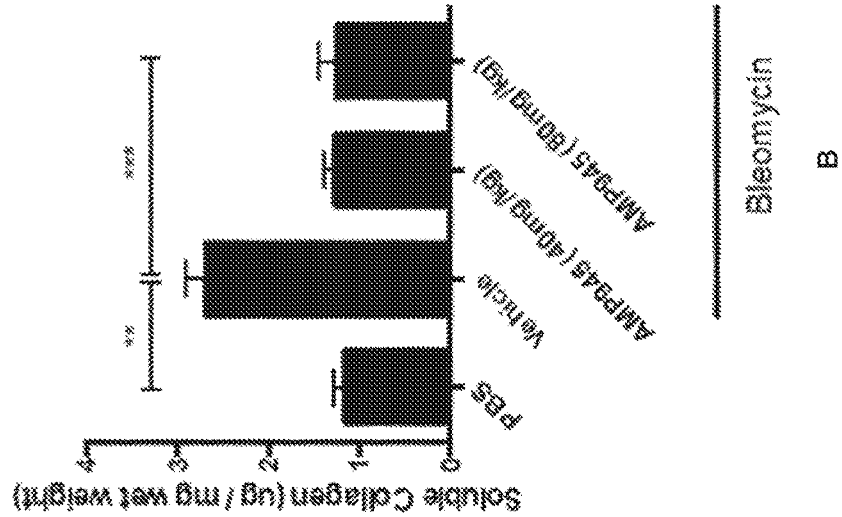
FIG. 3. Prevention Protocol. a) Measurement of mouse lung fibrosis on day 23 after treatment with PBS, bleomycin and vehicle, bleomycin and the compound of formula I 40 mg/kg or 80 mg/kg (n=8 mice per group). (a) The Ashcroft score was used to obtain a semi quantitative analysis of fibrosis (n=4 mice per group). (b) Acid-soluble collagen content in the mouse lung (n=8 mice per group). All bars represent the mean±SEM of n=4-8 mice as indicated. $*p<0.05$, $p\leq 0.01$ and $*p\leq 0.001$ by one-way ANOVA.
Figure 3:
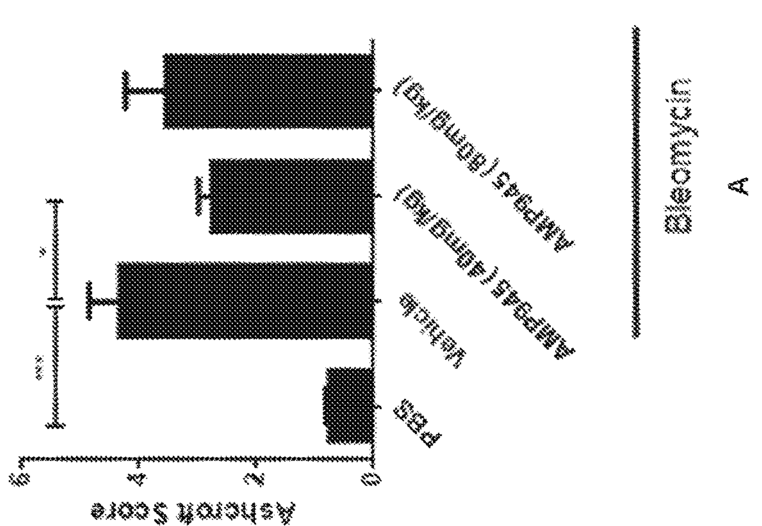

Prevention Model:

Intratracheal challenge with bleomycin did not cause a significant increase in lung weight at day 23 compared to PBS challenge but histological analysis revealed a highly significant increase in lung damage as assessed by the Ashcroft score (FIG. 2, bottom panels and FIG. 3*a*). The compound of Formula I dosed at 40 mg/kg but not at 80 mg/kg attenuated bleomycin-induced lung damage compared to vehicle (FIG. 3*a*).

Intra-tracheal bleomycin caused an increase in soluble lung collagen at day 23 (FIG. 3*b*). Oral administration of FAK inhibitor of Formula I inhibited soluble collagen levels to baseline (PBS) levels (FIG. 3*b*).

At a dose of 10 mg/ml methacholine, airways hyper-responsiveness (AHR) as assessed by airway and transpulmonary resistance, elastance and compliance was significantly greater in magnitude in mice that had been challenged with bleomycin compared to PBS (FIG. 5*a-d*). Treatment with the compound of Formula I at either 40 mg/kg or 80 mg/kg significantly decreased airways resistance compared to vehicle treatment. At 10 mg/ml methacholine, treatment with FAK inhibitors did not significantly inhibit other measures of AHR. However, compared to vehicle treatment, there was a trend towards the compound of Formula I being able to return AHR parameters to baseline (PBS challenge) levels.

Figure 4:
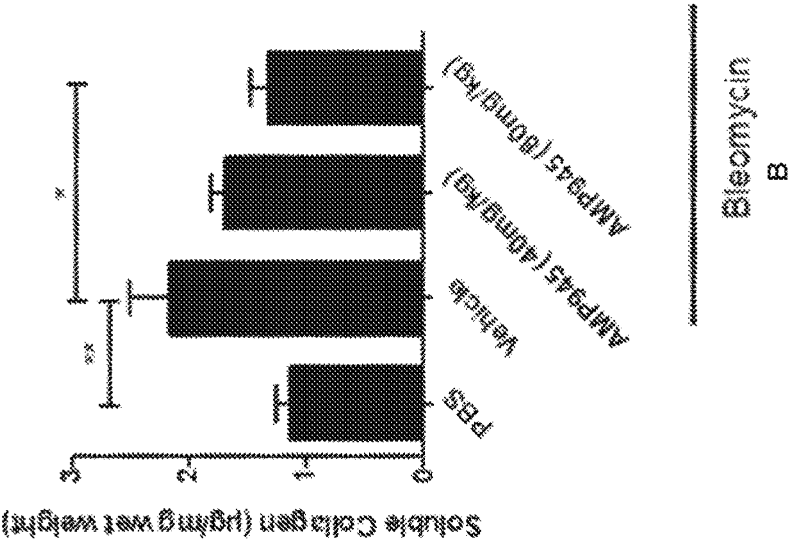
FIG. 4. Treatment Protocol. a) Measurement of mouse lung fibrosis obtained on day 22 after treatment with PBS, bleomycin and vehicle, bleomycin and compound of formula I 40 mg/kg or 80 mg/kg (n=8 mice per group). (a) The Ashcroft score was used to obtain a semi quantitative analysis of fibrosis (n=4 mice per group). (b) Acid-soluble collagen content in the mouse lung (n=8 mice per group). All bars represent the mean±SEM of n=4-8 mice as indicated. $^{*}p<0.05$ and $^{**}p\leq0.01$ by one-way ANOVA.
Figure 4:
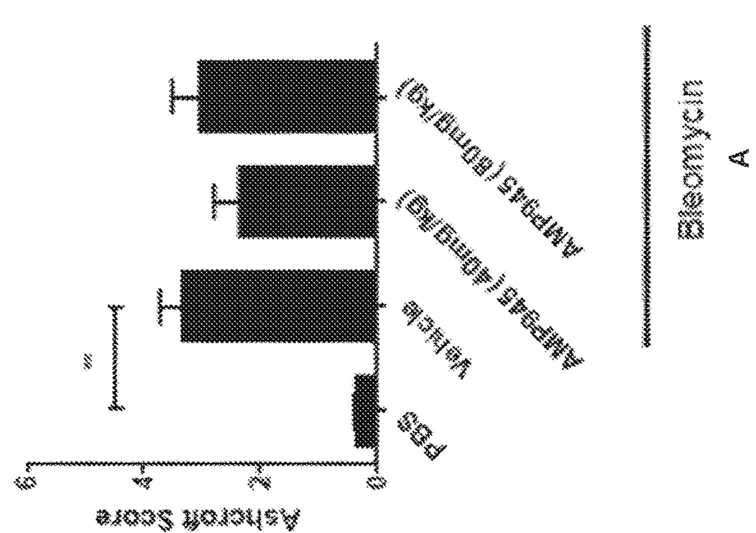

Treatment Model:

Intratracheal challenge with bleomycin did not cause a significant increase in lung weight at day 22 compared to PBS challenge. Histological analysis of mouse lung sections revealed a significant increase in lung damage as assessed by the Ashcroft score (FIG. 2 top panels and FIG. 4*a*). Administration of the compound of Formula I commencing 7 days following bleomycin exposure did not significantly alter bleomycin-induced lung damage compared to vehicle (FIG. 4*a*).

In the treatment model, intra-tracheal bleomycin caused an increase in soluble lung collagen at day 22 (FIG. 4*b*). The compound of Formula I 80 mg/kg inhibited soluble collagen levels compared to vehicle treatment (FIG. 4*b*).

Figure 5:
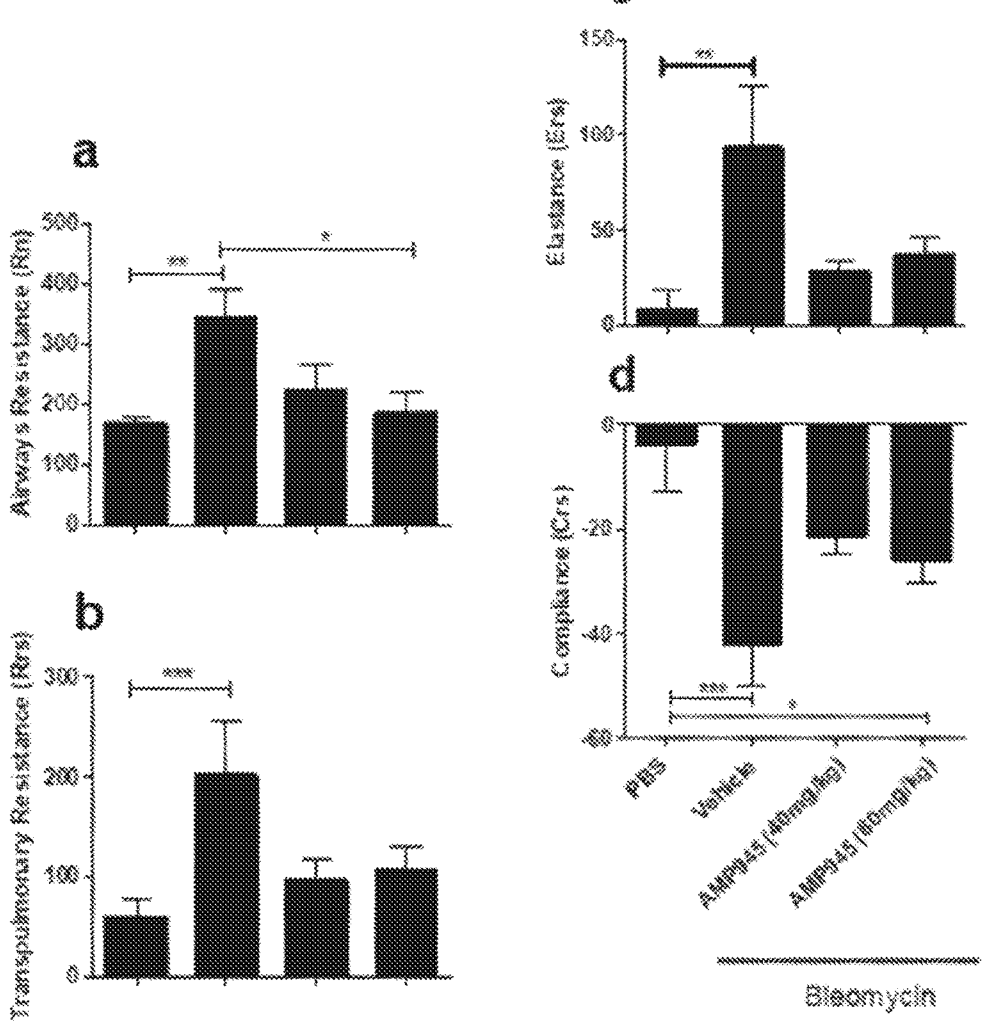
FIG. 5. Measurements of airways hyper-responsiveness (AHR) after methacholine challenge in the mouse lung. Panels (a)-(d) prevention protocol at day 23 after a single intra-tracheal dose with PBS or bleomycin and oral dosing with the compound of formula I as indicated. Panels (e)-(h) treatment protocol at day 22 after a single intra-tracheal dose with PBS or bleomycin and oral dose with the compound of formula I as indicated. Panels (a, e) show airways resistance, (b, f) transpulmonary resistance, (c, g) elastance, and (d, h) compliance following challenge with 10 mg/ml methacholine. All symbols and bars represent the mean±SEM of n=8 mice per group. $^{*}p\leq0.05$, $^{}p\leq0.01$ and $^{*}p\leq0.001$ by one-way ANOVA.

At a dose of 10 mg/ml methacholine, airways hyper-responsiveness (AHR) as assessed by airway and transpulmonary resistance, elastance and compliance was significantly greater in magnitude in mice that had been challenged with bleomycin compared to PBS (FIG. 5*e-h*). Treatment with the compound of Formula I had no effect on airways resistance compared to vehicle treatment (FIG. 5*e*). For all other measures of AHR, administration of the compound of Formula I commencing 7 days after bleomycin exposure effectively reversed the AHR to 10 mg/ml methacholine compared to vehicle treatment.

Taken together, the effects of the bleomycin model of lung fibrosis demonstrate that the compound of Formula I will provide a clinical benefit to patients with pulmonary fibrosis.

The invention claimed is:

1. A method of treating or preventing pulmonary fibrosis in a patient in need thereof by administering a FAK inhibitor defined by formula I or a pharmaceutically acceptable salt thereof to said patient:

Formula I

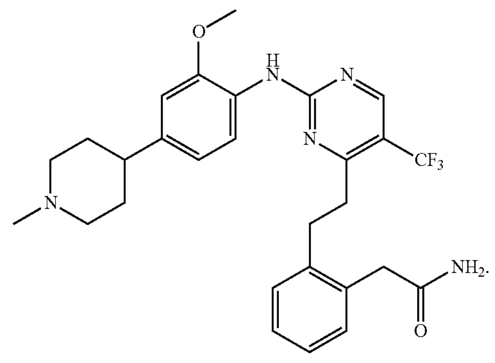

2. The method of claim 1 wherein said salt is a tartrate salt.

3. The method of claim 1 wherein the pulmonary fibrosis is idiopathic pulmonary fibrosis (IPF).

4. The method of claim 1 wherein the pulmonary fibrosis is associated with infection with a coronavirus.

* * * * *